United States Patent [19]
Waldman

[11] Patent Number: 5,342,365
[45] Date of Patent: Aug. 30, 1994

[54] SURGICAL RASP

[75] Inventor: Joel N. Waldman, Kansas City, Mo.

[73] Assignee: Padgett Instruments, Inc., Kansas City, Mo.

[21] Appl. No.: 92,990

[22] Filed: Jul. 19, 1993

[51] Int. Cl.$^5$ .............................................. A61B 17/00
[52] U.S. Cl. ............................................ 606/85; 29/78
[58] Field of Search ................. 606/85, 84; 29/78, 79, 29/80

[56] References Cited

U.S. PATENT DOCUMENTS

| | | |
|---|---|---|
| 30,996 | 6/1799 | Pegg . |
| 239,221 | 3/1876 | Wasserman . |
| 282,205 | 1/1886 | Davison et al. . |
| 343,136 | 6/1886 | Moore . |
| 349,490 | 9/1886 | Gallagher . |
| 1,002,468 | 9/1911 | Strangman . |
| 1,032,897 | 7/1912 | Hamilton . |
| 1,616,403 | 2/1927 | Womack . |
| 1,725,686 | 8/1929 | Ufer . |
| 2,082,685 | 6/1937 | Charlton . |
| 2,089,619 | 8/1937 | Ripley . |
| 2,363,769 | 11/1944 | Zipper ...................... 29/78 |
| 2,898,914 | 8/1959 | Sardal . |
| 3,016,771 | 1/1962 | Meissler et al. . |
| 3,045,509 | 7/1962 | Severance et al. . |
| 3,509,611 | 5/1970 | Kifer . |
| 3,605,527 | 9/1971 | Gambale . |
| 3,640,280 | 2/1972 | Slanker et al. . |
| 3,667,470 | 6/1972 | Rubin . |
| 3,815,599 | 6/1974 | Deyerle . |
| 4,182,204 | 1/1980 | Coon . |
| 4,584,745 | 4/1986 | Seiber ...................... 29/78 |
| 4,598,447 | 7/1986 | Whyde ...................... 29/78 |
| 4,625,725 | 12/1986 | Davison et al. ............ 606/85 |
| 5,027,519 | 7/1991 | DeVincentis ................ 29/78 |

FOREIGN PATENT DOCUMENTS

| | | |
|---|---|---|
| 1295606 | 10/1962 | France . |
| WO8300824 | 3/1983 | PCT Int'l Appl. . |
| 577391 | 5/1946 | United Kingdom . |
| 891403 | 3/1962 | United Kingdom . |

Primary Examiner—Tamara L. Graysay
Attorney, Agent, or Firm—Hovey, Williams, Timmons & Collins

[57] ABSTRACT

A surgical rasp is provided which includes a plurality of teeth each having a concave cutting face. The concave cutting face preferably provides an essentially self-sharpening tooth configuration for prolonging the useful life of the rasp. The rasp is preferably provided with a convex trailing face and an arcuate trough which aid in allowing removed tissue to move free of the rasp teeth. The rasp includes a handle presenting preferably a pair of opposed ends defining a longitudinal axis therebetween, with rows of teeth being provided on tungsten carbide inserts brazed or otherwise affixed to each of the ends.

3 Claims, 1 Drawing Sheet

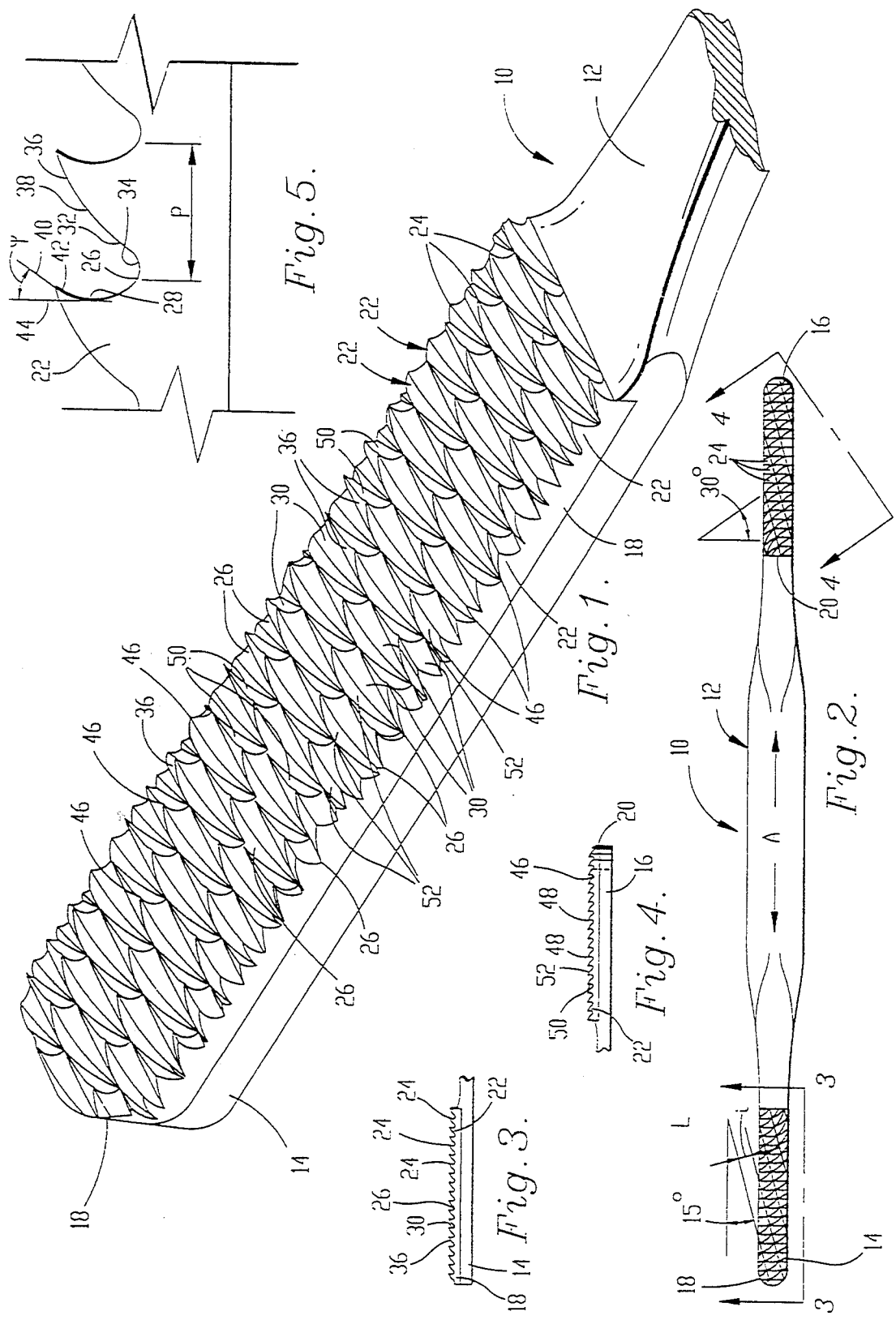

SURGICAL RASP

BACKGROUND OF THE INVENTION

1. Field of the Invention

This invention concerns a rasp for use primarily in plastic and reconstructive surgery which presents a novel tooth pattern and configuration for improved tissue removal. The aggressive tooth pattern is arranged to progressively span the width of the rasp thereby providing even results.

2. Description of the Prior Art

Rasps of the type described herein are used during plastic and reconstructive surgery to remove and shape tissue. These rasps may be used, for example, in rhinoplasty (nasal surgery), and consequently should be very precise in their construction, remain sharp to avoid excessive tearing of the flesh, and present even coverage across the cutting surface. Unfortunately, attaining these objectives has proven difficult and expensive.

One material used in making such rasps is tungsten carbide, which presents good hardness for maintaining a sharp edge. However, this hardness has also made the cutting face more difficult to machine. Rasps previously provided have presented teeth with a cutting face including teeth which were of limited aggressiveness to provide sharpness over an extended period. Thus, even using tungsten carbide as the material for a cutting surface or insert, sharpness can be lost over time when the cutting edge is exposed to wear. Of course, it must be recognized that the concept of sharpness is relative, and that surgical instruments must be extremely sharp to satisfy the needs of the medical community.

One other problem associated with various rasps concerns the accumulation of removed tissue between the individual rasp teeth. Such buildup can effectively "clog" the rasp and thus it is important that such rasps be configured so as to avoid trapping removed tissue between the teeth.

SUMMARY OF THE INVENTION

These objects have largely been solved by the surgical rasp in accordance with the present invention. The rasp hereof presents a novel tooth design which includes a leading face which is concave and terminates in a point which is positioned to lean forwardly in the direction that the rasp is drawn during use. The trailing face of the rasp tooth is convex, whereby the teeth present a "shark fin" appearance. As a result, wear on the cutting edge of each tooth has a much less pronounced effect on the rasp of the present invention as the narrowing of the apex yields more prolonged sharpness than in prior art tooth configurations.

In addition, the teeth of the rasp hereof, when viewed in section, present a trough with a curved surface between each of the teeth. A groove, also with a curved surface, is oriented at an angle to the trough to form individual teeth. The trough is of a radius which is sufficient to avoid substantial retention of tissue therein, whereby the tissue removed from the patient is removed from the file during use. The teeth are arrayed across the working portion of the rasp whereby substantially full coverage is achieved when the rasp is drawn in a direction parallel to its length.

The teeth are cut into a tungsten carbide insert affixed to a rasp handle. The teeth are formed by a first and second series of parallel transverse cuts extending at an angle relative to one another, thereby causing the points of the teeth in any row to progress across the top surface of the rasp. Such cuts are made by saws having blades with diamond teeth configured complementally to the tooth configuration of the present invention to present concave troughs and convex trailing faces.

BRIEF DESCRIPTION OF THE DRAWINGS

FIG. 1 is a perspective view of an insert for a rasp of the present invention, showing the tooth configuration hereof;

FIG. 2 is a plan view of the rasp hereof, with the 30 degree angle showing the direction of one transverse cut to form one trough and the 15 degree angle representing the orientation of the resulting point progression across the top face of the rasp insert;

FIG. 3 is a fragmentary side elevational view taken along line 3—3 of FIG. 2;

FIG. 4 is a fragmentary elevational view taken along line 4—4 of FIG. 2; and

FIG. 5 is an enlarged view of a section of the insert taken along either FIG. 3 or FIG. 4.

DESCRIPTION OF THE PREFERRED EMBODIMENT

Referring now to the drawing, a surgical rasp 10 as shown in FIG. 2 includes a handle 12 presenting a longitudinal axis A extending between ends 14 and 16. Inserts 18 and 20 are positioned at respective ends 14 and 16. The inserts are made of a suitably hard, wear-resistant material such as tungsten carbide, and affixed to the handle by any suitable means such as, e.g., brazing. Each insert 18 and 20 defines a number of teeth 22 thereon for removing tissue during surgery.

The teeth 22 are presented in adjacent parallel rows 24 which are oriented transversely to the longitudinal axis A. Preferably, the rows 24 are aligned perpendicular to the longitudinal axis A whereby the tissue is scraped evenly when the rasp 10 is pulled along axis A. The rows 24 are provided by cutting a trough 26 at an angle to the axis A corresponding to the desired alignment of the rows, and in particular in a perpendicular direction relative to the axis A. Each trough 26, seen in greater detail in FIG. 5, is substantially arcuate. The trough 26 defines an arcuate concave surface 28 on the cutting face 30 and an arcuate concave surface 32 at the base 34 of the trailing face 36 of the next tooth in the adjacent row 24. The pitch P of the rasp 10 is about 1.5 to 2.5 mm, and preferably about 2 mm for most plastic surgery applications, and in such instances the radius of curvature would be about 1.5 and 1.4 mm, respectively for the surfaces 28 and 32. Each tooth 22 also includes a convex surface 38 on the trailing face 36 located nearer the apex 40 than the concave surface 32. Again, when P is about 2 mm, the radius of curvature of the convex surface 38 is preferably about 1.7 mm. The cutting face 30 also includes a cutting crest 42 which is located immediately adjacent the apex 40, and is oriented at an angle psi which extends forwardly between about 4° and 10° relative to a plane 44 extending perpendicular to the surface of the respective insert.

In addition, a series of parallel grooves 46 are cut into the inserts 18 and 20 at an angle to both the axis A and the trough 26. Each groove 46 is preferably cut at an angle of about 30° to the troughs 26 which are perpendicular relative to the longitudinal axis A at a spacing index i which is equal to P, i.e. about 2 mm, whereby ranks 48 of teeth 22 are formed at an angle to rows 24.

The teeth 22 in adjacent rows 24 are thereby staggered laterally across the inserts to provide good lateral coverage for cutting evenly as the rasp is drawn toward the surgeon. When viewed along the ranks 48 as shown in FIG. 4, a third side face 50 which is generally concave is presented, as well as a fourth side face 52 which is generally convex. The third side face 50 and the fourth side face 52 preferably present the same appearance when viewed along line 4—4 as do cutting face 30 and trailing face 36 respectively. Thus, the appearance of the teeth 22 as shown in FIG. 5 reflects the appearance of the teeth when viewed along the ranks 48 as well as along the rows 24 so that the third face 50 presents a mirror image of the cutting face 30 and the fourth face 52 presents a mirror image of the trailing face 36 about a vertical plane along line L oriented at an angle of 15° relative to the longitudinal axis A as shown in FIG. 2.

The rows 24 and the ranks 48 are formed when the parallel troughs 26 and the parallel grooves 46 are cut into the tungsten carbide inserts 14 and 16 by a saw having a diamond blade. The blade is configured to cut the insert to provide the trough and groove configuration as shown and described. The concave cutting face 30 preferably faces toward the center or handle 12 of the surgical rasp 10 hereof, whereby the surgeon may draw the rasp toward him to smooth the bone or other tissue, as opposed to pushing the rasp. Thus, the concave cutting faces 30 of each insert are opposed to one another. The inserts 18 and 20 may present teeth 22 having different effective heights, degrees of concavity or forward angling of the crests, or other characteristics which would allow the surgeon to reverse the ends 14 and 16 during use as circumstances dictate.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of his invention as pertains to any apparatus not materially departing from but outside the liberal scope of the invention as set out in the following claims.

I claim:

1. A surgical rasp comprising a handle having a longitudinal axis and an insert rigidly affixed to the handle at one end thereof, said insert presenting a cutting surface having a plurality of teeth thereon, wherein the improvement comprises:

a plurality of teeth defining said cutting surface, said teeth being arranged in adjacent parallel rows oriented transversely to the longitudinal axis and in adjacent parallel ranks oriented at an angle to said rows, said teeth presenting a first smoothly concave cutting face oriented substantially perpendicular to said longitudinal axis and defined by an arcuate concave trough in said insert parallel to and separating said rows, a second smoothly convex trailing face in opposition to said first face, a third smoothly concave side face oriented at an obtuse angle to said first face, said third face being substantially a mirror image of said first face and defined by a transverse arcuate concave groove in said insert parallel to and separating said ranks, and a fourth smoothly convex side face oriented at all obtuse angle to said second face, said fourth face being substantially a mirror image of said second face, said first face and said third face each including a concave cutting crest extending forwardly toward its respective trough and groove, said first face, second face, third face and fourth face extending upwardly to converge and terminate in an uppermost apex with the first face and third face being substantially continuously concave from a base of each trough and groove to the apex and the second face and the fourth face being substantially continuously convex from the base of each trough and groove to the apex.

2. A surgical rasp as set forth in claim 1, wherein said handle presents first and second longitudinally opposed ends each carrying one of said inserts having a plurality of said teeth thereon.

3. A surgical rasp as set forth in claim 2, where said teeth are oriented in opposition with the first face of said teeth at said first end are in facing orientation to the first face of said teeth at said second end.

* * * * *